(12) United States Patent
Berberich et al.

(10) Patent No.: US 8,640,539 B2
(45) Date of Patent: Feb. 4, 2014

(54) DEVICE FOR TREATING SPECIMENS AND METHOD FOR DETERMINING THE FILL LEVEL OF REAGENT CONTAINERS

(75) Inventors: Markus Berberich, Heidelberg (DE); Benjamin Siehl, Nussloch (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 487 days.

(21) Appl. No.: 12/683,725

(22) Filed: Jan. 7, 2010

(65) Prior Publication Data

US 2010/0170336 A1 Jul. 8, 2010

(30) Foreign Application Priority Data

Jan. 8, 2009 (DE) .......................... 10 2009 004 043

(51) Int. Cl.
*G01F 23/296* (2006.01)
*G01N 1/31* (2006.01)
(52) U.S. Cl.
USPC .......................... 73/290 V; 73/290 R; 422/65
(58) Field of Classification Search
None
See application file for complete search history.

(56) References Cited

U.S. PATENT DOCUMENTS

| | | | |
|---|---|---|---|
| 3,894,438 A | 7/1975 | Ginsberg | |
| 5,880,364 A | 3/1999 | Dam | |
| 6,572,824 B1 * | 6/2003 | Ostgaard et al. | ................. 422/67 |
| 7,472,593 B2 * | 1/2009 | Tenney | ........................ 73/290 R |
| 2002/0090730 A1 | 7/2002 | Eckert et al. | |
| 2002/0121139 A1 | 9/2002 | Purpura et al. | |
| 2007/0012113 A1 | 1/2007 | Ulmer | |
| 2007/0125170 A1 | 6/2007 | Tenney | |

FOREIGN PATENT DOCUMENTS

| | | |
|---|---|---|
| EP | 0979999 A2 | 2/2000 |
| EP | 1153882 A1 | 11/2001 |
| JP | 1981021744 | 2/1981 |
| JP | 1984154632 | 10/1984 |
| JP | 1989049207 | 3/1989 |
| JP | 09203737 A | 8/1997 |
| JP | 10253638 | 9/1998 |
| JP | 1183867 | 3/1999 |
| JP | 2000321189 A | 11/2000 |
| JP | 2000321289 | 11/2000 |
| JP | 2001021468 | 1/2001 |

* cited by examiner

*Primary Examiner* — Yelena G Gakh
*Assistant Examiner* — Michelle Adams
(74) *Attorney, Agent, or Firm* — Hodgson Russ LLP

(57) ABSTRACT

The invention relates to a device (10) for treating specimens, comprising a plurality of reagent containers (12) which are arranged in predetermined positions. Further, the device (10) comprises a transport mechanism (22a, 22b) for transporting at least one transport container (16a, 16b) which accommodates at least one carrier (20). On the carrier at least one specimen is placed. Further, the device (10) has a sensor (34) for determining the fill level (44) of the reagent containers (12) with reagents (42), the sensor (34) being arranged on the transport mechanism (22a, 22b). Further, the invention relates to a method for determining the fill level (44) of reagent containers (12) with reagents (42).

6 Claims, 2 Drawing Sheets

Figure 1:
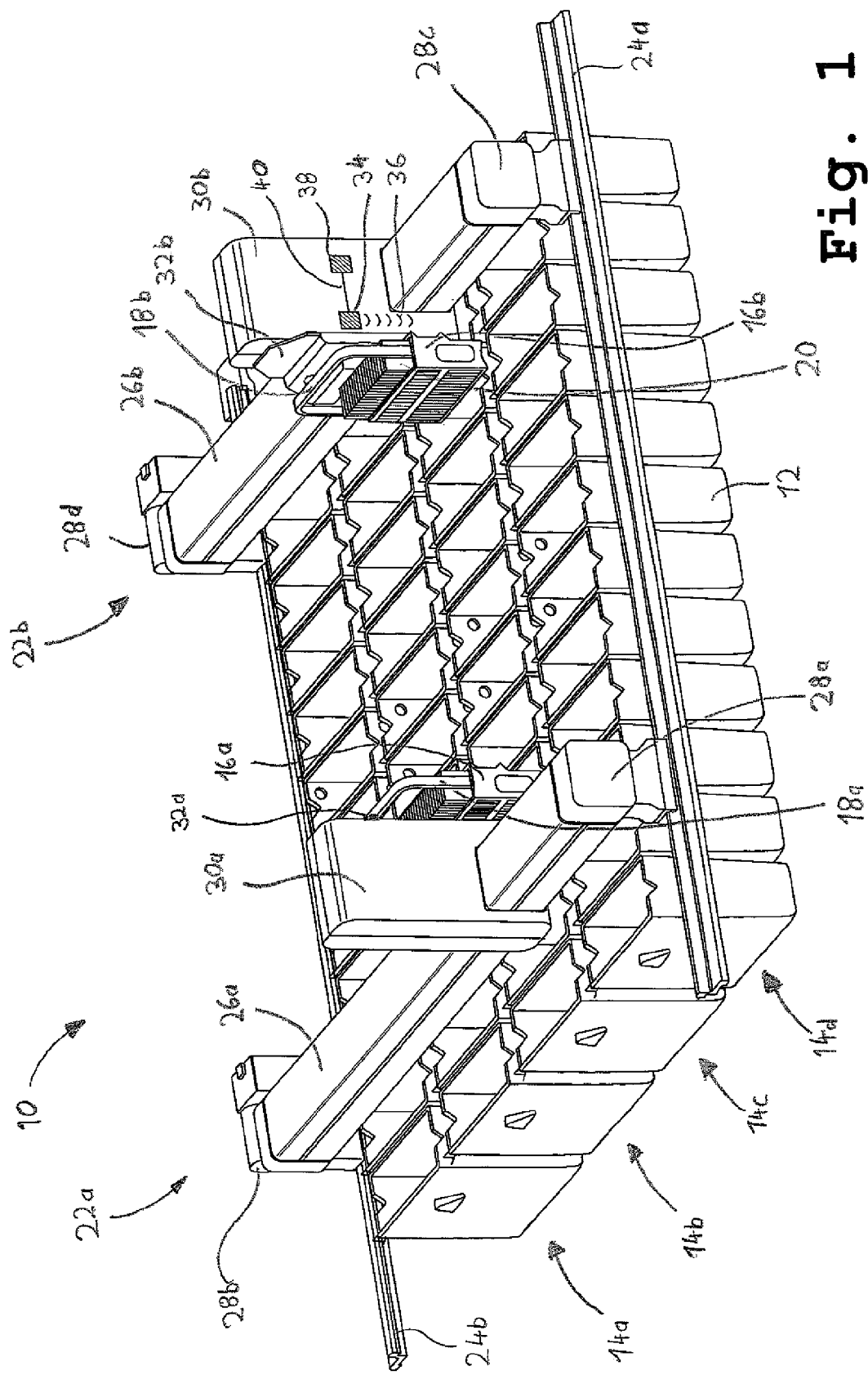

DEVICE FOR TREATING SPECIMENS AND METHOD FOR DETERMINING THE FILL LEVEL OF REAGENT CONTAINERS

CROSS REFERENCE TO RELATED APPLICATIONS

This application claims priority of the German patent application 10 2009 004 043.9 filed Jan. 8, 2009, which application is incorporated by reference herein.

FIELD OF THE INVENTION

The invention relates to a device for treating specimens, comprising a plurality of reagent containers which are arranged in predetermined positions. Further, the device comprises a transport mechanism for transporting at least one transport container which accommodates at least one carrier. At least one specimen is placed on the carrier. Further, the invention relates to a method for determining the fill level of reagent containers with reagents.

BACKGROUND OF THE INVENTION

The device and the method are preferably used in histology. Histology deals with the examination of tissue samples from patients. The most common procedure is that the tissue samples are taken from the patients, embedded in paraffin, thin sections are cut with the aid of a microtome from the specimen blocks produced in this way, and one thin section each is placed on one carrier each. Subsequently, in a further process the specimens are treated, in particular dyed, before they are supplied to a microscope for diagnostic evaluation.

During the treatment, the carriers on which the specimens are placed are immersed with the aid of a transport container and a transport mechanism in a reagent container filled with reagent, and are left therein for a predetermined time before they are taken out of the reagent container and are transported with the aid of the transport mechanism into another reagent container. The control of this treatment process is preferably effected computer-controlled. It is important that the reagent containers are each filled with the correct amount of reagents. When the reagent container is filled with too much reagent, then it may happen that the reagent spills over the reagent container owing to the displacement of the reagent by the transport container and the carriers. The result is that the device for treating the specimens and/or the surrounding area is contaminated. It is particularly critical when other reagent containers are contaminated by the reagent spilled over a too full reagent container. This is particularly the case given devices in which the reagent containers are arranged above one another in several planes. In order to prevent such a contamination of one reagent container by the reagent of another reagent container, reagent containers having a defined mechanical overflow are used in the prior art, through which overflow the reagent can run off in a controlled manner in case of overfilling, and a contamination of other reagent containers, the device and/or the surrounding area is avoided. What is disadvantageous here is that by means of the mechanical overflow, relief is only given in case of an overfilling of the reagent container. It is, however, likewise critical when a reagent container is not filled with sufficient reagent so that the specimens immersed in the reagent container are not or not completely covered with the reagent so that the desired treatment of the specimens is not guaranteed.

SUMMARY OF THE INVENTION

It is the object of the invention to specify a device for treating specimens and a method in which the fill level of at least one reagent container with reagents can easily be determined.

This object is solved by a device having the features described herein and a method described herein. Advantageous developments of the invention are also described.

According to the invention, the device for treating the specimens comprises at least one sensor for determining the fill level of the reagent container with reagents. The sensor is arranged on the transport mechanism for transporting the transport container. This makes possible that with the aid of only one sensor the fill level of all reagent containers arranged in the device can be determined.

It is advantageous when the determination of the fill level with the aid of the sensor is made in a contact-free manner. Thus, a contamination of the sensor is prevented, as a result whereof potential errors in the determination of the fill level are prevented. The required maintenance of the sensor is reduced as well.

It is particularly advantageous when the sensor is an ultrasonic sensor. Such an ultrasonic sensor is a common standard part, and can thus be obtained in a cost-efficient manner.

Further, it is advantageous to provide an evaluation unit for evaluating the information determined with the aid of the sensor. This makes possible that the device for treating specimens does not have to be connected to an external evaluation unit, in particular a computer. Thus, a compact, cost-efficient construction of the device is made possible, and the device can be transported between different locations, without it being necessary that further devices for evaluating the information determined with the aid of the sensor have to be transported as well or have to be provided more than once.

Preferably, the sensor is arranged on the transport mechanism such that with the aid of the sensor the fill level of a reagent container can be determined before the transport container is moved into this reagent container. This makes possible that the transport container with the carriers is not immersed in the reagent containers at all when the evaluation of the information on the fill level of the reagent container generated with the aid of the sensor provides that the fill level of the reagent container does not lie within a predetermined range. Thus, it is, for example, avoided that the specimens placed on the carrier are only partially dyed, and thus are useless.

In addition, it is advantageous when the sensor is arranged on the transport mechanism such that the vertical distance to the reagent containers is constant. As a result thereof, the expense for determining the fill level of the reagent container is reduced.

Further, it is advantageous when a control unit for controlling the transport mechanism is provided and when this control unit controls the transport mechanism such that a transport container is only moved into a reagent container when the fill level of the reagent container determined with the aid of the sensor is at least as high as a predetermined minimum fill level. As a result thereof, it is prevented that the specimens placed on the carriers of the transport container are only partially treated, and thus become useless.

Preferably, an output unit for outputting to a user at least one piece of information generated depending on the fill level of at least one reagent container is provided. This piece of information can, for example, be a signal that informs the user when the fill level of the reagent container into which the transport container is to be immersed does not lie within the predetermined range, and requests the user to adapt the fill level of the reagent container accordingly. Preferably, the output unit is a screen.

Alternatively or additionally, with the aid of this output unit the fill level of one or more reagent containers can be continuously displayed to the user so that the user can preventively intervene in due time before the fill level of one or more reagent containers goes beyond the admissible range, and the device can thus no longer be operated or only continued to be operated in a limited way.

A further aspect of the invention relates to a method for determining the fill level of reagent containers with reagents in which with the aid of a sensor the fill level of at least one reagent container is determined. The sensor is moved with the aid of a transport mechanism above those reagent containers whose fill level is to be determined.

It is advantageous when the sensor generates one signal each with information on the fill level of each of the reagent containers, transfers the signal to an evaluation unit, and the signal is compared to a predetermined minimum fill level with the aid of the evaluation unit. As a result thereof, it can easily be detected when a reagent container is no longer sufficiently filled with reagent. The signal is preferably an electric signal.

It is particularly advantageous when the transport mechanism is controlled with the aid of a control unit such that a transport container is only moved into the reagent container when the fill level of the reagent container determined with the aid of the sensor is at least as high as the predetermined minimum fill level. In this way, it is avoided that specimens are only partially covered and treated with reagent, and thus are no longer of use for the further evaluation.

Further, it is advantageous when the transport mechanism is controlled with the aid of a control unit such that a transport container is only moved into the reagent container when the fill level of the reagent container determined with the aid of the sensor is at most as high as a predetermined maximum fill level. As a result thereof, an overflow of the reagent container in which the transport container is immersed is prevented.

Further, it is advantageous when at least one piece of information generated depending on the fill level of at least one reagent container is output to a user with the aid of an output unit. It is particularly advantageous when the fill level of at least one reagent container is output to the user and/or a piece of information is output to the user when the fill level of the reagent container determined with the aid of the sensor is less than the minimum fill level stored in the evaluation unit. As a result thereof, it is achieved that the user can intervene promptly in that he/she fills the reagent container or the reagent containers at least with so much reagent that the minimum fill level is reached, and the treatment of the specimens only has to be interrupted for a short amount of time.

The method specified by the independent method claim can be developed in the same manner as the device according to claim 1. In particular, the method can be further developed by the features specified in the claims dependent on the device or by corresponding method features.

BRIEF DESCRIPTION OF THE DRAWING VIEWS

Further features and advantages of the invention result from the following description which in connection with the enclosed figures explains the invention in more detail with reference to embodiments.

Figure 2:
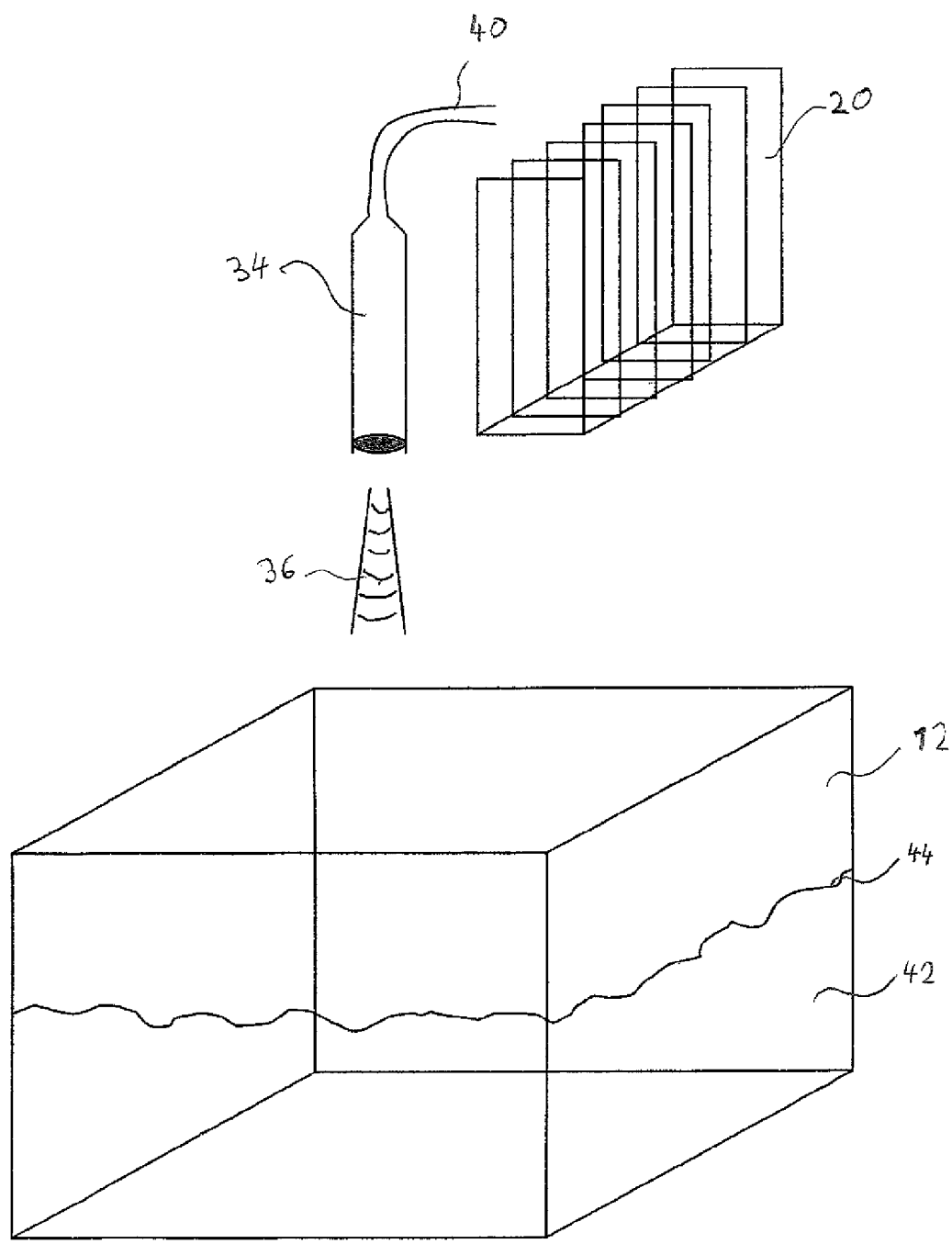

FIG. 1 shows a perspective view of a schematic illustration of a device for treating specimens; and FIG. 2 shows a perspective schematic illustration of a detail of the device according to FIG. 1.

DETAILED DESCRIPTION OF THE INVENTION

In FIG. 1, a schematic view of a device 10 for treating specimens is shown. The device 10 comprises a plurality of reagent containers which are arranged in predetermined positions. One of these reagent containers is exemplarily identified with the reference numeral 12. The reagent containers 12 are also referred to as cuvettes. In the present embodiment according to FIG. 1, the reagent containers 12 are arranged in four container rows 14a to 14d. The reagent container rows 14a to 14d are arranged parallel to one another so that altogether a matrix-shaped arrangement of the reagent containers 12 results. In their entirety in the matrix-shaped arrangement, the reagent containers 12 are also referred to as a reagent container field or cuvette field.

In alternative embodiments of the invention, the reagent containers 12 can also be differently arranged. In particular the reagent containers 12 can be arranged above one another in several planes.

The reagent containers 12 are filled with reagents which, for example, serve to dye specimens. Such reagents can in particular be solutions, coloring solutions or water.

Further, two transport containers 16a, 16b are shown in FIG. 1. The transport containers 16a, 16b are preferably transport baskets 16a, 16b, also referred to as racks. The respective width of a transport container 16a, 16b approximately corresponds to the length of a reagent container 12. Each transport container 16a, 16b comprises a bail 18a, 18b on its upper end. The transport containers 16a, 16b are formed such that the bail 18a, 18b projects from the reagent container 12 when the transport container 16a, 16b is inserted into the reagent container 12.

The transport containers 16a, 16b can each accommodate one carrier. One of these carriers is exemplarily identified with the reference numeral 20. The carriers 20 are in particular glass carriers, which are also referred to as slides. On each carrier 20, at least one specimen to be treated each is placed. These specimens are in particular thin sections of biological material.

The treatment of the specimens, in particular the dying of biological material, takes place in that a transport container 16a, 16b is inserted in a reagent container 12, left therein for a predetermined amount of time, subsequently taken out of the reagent container 12, transported to a further reagent container 12 and is inserted therein. This procedure can take place several times during the treatment of a specimen.

The transport of the transport containers 16a, 16b from one reagent container 12 to another reagent container 12 takes place with the aid of a transport unit 22a, 22b. In the illustrated embodiment, the device 10 comprises two transport units 22a, 22b for the transport of the transport containers 16a, 16b, wherein the two transport units 22a, 22b can simultaneously transport containers 16a, 16b. Alternatively, the device 10 can also comprise only one transport unit 22a, 22b.

The two transport units 22a, 22b are mounted on two rails 24a, 24b. The rails 24a, 24b are arranged parallel to one another on two opposite sides of the cuvette field. Each transport unit 22a, 22b comprises one first linear axis 26a, 26b. On each of the ends of the first linear axis 26a, 26b, one slide 28a to 28d is arranged. One slide 28a, 28c each of each transport unit 22a, 22b rests on the first rail 24a. The respective slides 28b, 28d arranged on the opposite end of the respective linear axis 26a, 26b rest on the other rail 24b. By displacing the slides 28a to 28d on the rails 24a, 24b, the transport units 22a, 22b can be moved in the direction of an x-axis. The linear axes 26a, 26b run orthogonally to the x-axis in the direction of an y-axis.

The transport units 22a, 22b each comprise a transport slide 30a, 30b which is moveably mounted in the direction of the y-axis on the respective linear axis 26a, 26b. The transport slides 30a, 30b each comprise a gripper 32a, 32b on the side facing the respective other transport unit 22a, 22b. The grippers 32a, 32b are displaceable in the direction of a z-axis which runs orthogonally to the x-axis and orthogonally to the y-axis.

If a transport container 16a, 16b is to be transported, then the gripper 32a, 32b is moved such that at least a part of the gripper 32a, 32b is located below the bail 18a, 18b of the transport container 16a, 16b to be transported. Subsequently, the gripper 32a, 32b is lifted, the gripper 32a, 32b engaging below the bail 18a, 18b of the transport container 16a, 16b to be transported. The transport container 16a, 16b to be transported is subsequently lifted with the aid of the gripper 32a, 32b until the lower end of the transport container 16a, 16b is located above the reagent container 12 from which the transport container 16a, 16b has been taken. Subsequently, the transport container 16a, 16b is moved with the aid of the respective transport unit 22a, 22b in the direction of the x- and/or y-axis until it is located above the reagent container 12 in which the transport container 16a, 16b is to be immersed. The gripper 32a, 32b and the transport container 16a, 16b held by the gripper are moved downwards in the direction of the z-axis in the direction of the reagent container 12 until the transport container 16a, 16b comes to rest on the ground of the reagent container 12. The gripper 16a, 16b is preferably moved a little bit further down and subsequently moved out in the direction of the x-axis beneath the bail 18a, 18b of the transport container 16a, 16b.

In the embodiment, the transport mechanism formed by the two rails 24a, 24b and the two transport units 22a, 22b is a linear transport mechanism with three linear axes that are orthogonally with respect to one another. Alternatively, other transport mechanisms are likewise possible.

Each transport unit 22a, 22b comprises one sensor 34 each. The sensor of the first transport mechanism 22a is not visible in FIG. 1 since it is covered by the transport slide 30a. With the aid of the sensor 34, the fill level of reagent containers with reagent can be determined. When dying the specimens placed on the carriers 20, it is important that the respective reagent containers 12 are each filled with the correct amount of reagent. If one reagent container 12 contains too much reagent, then the reagent container 12 can spill over during the insertion of the transport container 16a, 16b owing to the displacement of the reagent by the transport container 16a, 16b and the carriers 20 included in the transport container 16a, 16b. As a result thereof, the device 10 and/or the surrounding area can be contaminated. Given devices in which the reagent containers 12 are arranged above one another in several planes, the overflow of a reagent container 12 can result in a contamination of the reagent present in a reagent container 12 arranged underneath.

If there is too little reagent in the reagent container 12, then it can be that the specimens placed on the carriers 20 are not or not completely covered with the reagent when the carriers 20 are inserted into the reagent container 12 by means of the transport container 16a, 16b. As a result thereof, the specimen is not or at least not completely dyed and is no longer suitable for further use, in particular the microscopic examination. Reasons for a too low fill level of a reagent container can, for example, be that the reagent has been used up or that a user has forgotten to fill the reagent container 12 or has filled up the wrong reagent container 12. Therefore, the fill level of a reagent container 12 must be between a predetermined minimum fill level and a likewise predetermined maximum fill level.

The sensor 34 is arranged on the transport slide 30b of the second transport unit 22b such that by means of the sensor 34 data with information on the fill level of a reagent container 12 can be generated before a transport container 16a, 16b is immersed in this reagent container 12. The determination of the data with information on the fill level of the reagent container 12 is made in a contact-free manner. In this way, contaminations of the sensor 34 are avoided and cleaning and maintenance work can be minimized. The sensor 34 for determining the fill level is in particular an ultrasonic sensor 34. The ultrasonic waves emitted by the ultrasonic sensor 34 are indicated in FIG. 1 by the lines 36. What is achieved by the arrangement of the sensor 34 on the transport slide 30b is that the distance between the sensor 34 and the reagent containers 12 is constant. In this way, the fill level of the reagent container 12 can be determined with little expense.

The above explanations apply accordingly to the first transport unit 22a.

In alternative embodiments of the invention, several sensors 34 for determining the fill level can be arranged on a transport slide 30a, 30b. Alternatively, it is likewise possible that the sensor 34 is arranged on the linear axis 26a, 26b.

In a further alternative embodiment of the invention, the sensor 34 can be moved by means of an own transport mechanism above the reagent container field.

Further, each transport unit 22a, 22b comprises an evaluation unit 38. The evaluation unit 38 is likewise arranged on the transport slide 30a, 30b and is connected to the sensor 34 via a suitable line 40 for transferring the data with the information on the fill level of the reagent container 12 generated by the sensor 34. The data generated by means of the sensor 34 are in particular electric signals which are transferred via an electric line 40 to the evaluation unit 38. This electric signal preferably lies within the range between 4 and 20 mA and is proportional to the predetermined maximum fill level.

By means of the evaluation unit 38, the information generated by means of the sensor 34 is evaluated. In particular, the fill level determined by means of the sensor 34 is compared to the predetermined minimum fill level stored in the evaluation unit and the predetermined maximum fill level likewise stored in the evaluation unit. When the comparison of the determined fill level to the minimum fill level and the maximum fill level shows that the reagent container 12 in which the transport container 16a, 16b is to be immersed is filled too much or too little with reagent, the transport container 16a, 16b is not immersed in the reagent container 12. Preferably, the prevention of the immersion of the transport container 16a, 16b in the reagent container 12 takes place automatically in that a program is stopped which is executed by a non-illustrated control unit for controlling the device 10, and in which it is stored in which sequence which transport containers 16a, 16b have to be immersed in which reagent containers 12 and how long the respective transport containers 16a, 16b have to be left in the respective reagent containers 12. The treatment of the specimens arranged in the transport container 16a, 16b is only continued when the fill level of the reagent container 12 has been corrected such that the fill level lies between the minimum fill level and the maximum fill level.

Additionally or alternatively, a piece of information generated depending on the determined fill level can be output to the user via a non-illustrated output unit. In particular, it can be displayed to the user when the fill level of a reagent container 12 lies below the minimum fill level or above the maximum fill level, and the user can be requested to adapt the fill level of the respective reagent container 12 accordingly. Additionally or alternatively, the user can be informed by an acoustic signal.

Additionally or alternatively, the fill level of a reagent container or of several reagent containers can likewise be output to the user by means of the output unit. The output unit is preferably a screen. In this way, the current fill level of the respective reagent containers 12 is continuously displayed to the user so that he can preventively intervene before the fill level of a reagent container 12 falls below the minimum fill level. By re-filling this reagent container 12 in due time it can be avoided that the treatment of the specimen has to be interrupted. In this way, downtimes of the device 10 can be avoided or at least reduced.

Further, the fill level of the reagent containers 12 can be additionally or alternatively transferred to a non-illustrated central evaluation unit and thus be made accessible to the further processing.

In FIG. 2, a perspective schematic illustration of a detail of the device 10 according to FIG. 1 is shown. Elements having the same structure or the same function are identified with the same reference signs.

The reagent container 12 is filled with a reagent 42. The fill level of the reagent container 12 with the reagent 42 is indicated by the line 44. The fill level of the reagent container 12 is determined by means of the ultrasonic sensor 34 before the carrier 20 is immersed in the reagent container 12.

LIST OF REFERENCE SIGNS 10 device
12 reagent container
14a, 14b, 14c, 14d reagent container row
16a, 16b transport container
18a, 18b bail
20 carrier
22a, 22b transport unit
24a, 24b rails
26a, 26b linear axis
28a, 28b, 28c, 28d slide
30a, 30b transport slide
32a, 32b gripper
34 sensor
36 ultrasonic waves
38 evaluation unit
40 line
42 reagent
44 fill level

What is claimed is:

1. A device for treating specimens, comprising:
a plurality of reagent containers (12) which are arranged in predetermined positions, the plurality of reagent containers (12) being filled with reagents at a fill level (44),
a transport mechanism (22a, 22b) for transporting at least one transport container (16a, 16b) which accommodates at least one carrier (20) on which at least one specimen can be placed,
at least one sensor (34) for determining the fill level (44) of the plurality of reagent containers (12) with reagents (42), the at least one sensor being separated from the plurality of reagent containers by a vertical distance, and
an evaluation unit (38) for evaluating information determined by the at least one sensor (34),
wherein the transport mechanism (22a, 22b) comprises a gripper (32a, 32b) by which the at least one transport container (16a, 16b) can be moved into one of the plurality of reagent containers (12) and out of the one of the plurality of reagent containers (12), respectively,
wherein the at least one sensor (34) is arranged on the transport mechanism (22a, 22b) such that the vertical distance from the at least one sensor to the plurality of reagent containers (12) is constant during upward and downward movement of the at least one transport container by the gripper,
wherein a vertical distance between the gripper and the plurality of reagent containers changes during the upward and downward movement of the at least one transport container by the gripper.

2. The device according to claim 1, wherein the at least one sensor (34) is a non-contact sensor for determining the fill level (44) in a contact-free manner.

3. The device according to claim 2, wherein the at least one sensor (34) is an ultrasonic sensor.

4. The device according to claim 1, wherein in a first position, the at least one transport container (16a, 16b) is out of the one of the plurality of reagent containers (12), and in a second position the transport container (16a, 16b) is moved into the one of the plurality of reagent containers (12)
wherein the at least one sensor (34) is arranged on the transport mechanism (22a, 22b) such that by operation of the at least one sensor (34), the fill level (44) of the one of the plurality of reagent containers (12) is determinable in the second position.

5. The device according to claim 4, further comprising a control unit for controlling the transport mechanism (22a, 22b) such that a transport container (16a, 16b) is only moved into the one of the plurality of reagent containers (12) when the fill level (44) of the one of the plurality of reagent containers (12) determined by the at least one sensor (34) is at least as high as a predetermined minimum fill level.

6. The device according to claim 1, further comprising an output unit for outputting to a user at least one piece of information generated depending on the fill level (44) of at least one of the plurality of reagent containers (12).

* * * * *